United States Patent
Childress

(10) Patent No.: US 12,337,071 B2
(45) Date of Patent: Jun. 24, 2025

(54) ROTATING DISINFECTING DEVICE THAT INCLUDES ULTRAVIOLET EMITTERS

(71) Applicant: The Boeing Company, Chicago, IL (US)

(72) Inventor: Jamie J. Childress, Mercer Island, WA (US)

(73) Assignee: THE BOEING COMPANY, Arlington, VA (US)

( * ) Notice: Subject to any disclaimer, the term of this patent is extended or adjusted under 35 U.S.C. 154(b) by 927 days.

(21) Appl. No.: 17/366,466

(22) Filed: Jul. 2, 2021

(65) Prior Publication Data

US 2022/0111088 A1 Apr. 14, 2022

Related U.S. Application Data

(60) Provisional application No. 63/089,112, filed on Oct. 8, 2020.

(51) Int. Cl.
*A61L 2/10* (2006.01)
*A61L 2/26* (2006.01)

(52) U.S. Cl.
CPC .................... *A61L 2/10* (2013.01); *A61L 2/26* (2013.01); *A61L 2202/11* (2013.01); *A61L 2202/25* (2013.01)

(58) Field of Classification Search
CPC ........... A61L 2/10; A61L 2/26; A61L 2202/11
See application file for complete search history.

(56) References Cited

U.S. PATENT DOCUMENTS

| | | | |
|---|---|---|---|
| 2002/0190220 A1* | 12/2002 | Sarchese | A61L 2/10 250/432 R |
| 2016/0121007 A1* | 5/2016 | Dayton | A61L 2/10 250/492.1 |
| 2017/0326262 A1 | 11/2017 | Paver, Jr. | |
| 2018/0256764 A1* | 9/2018 | Kreitenberg | A61L 9/20 |
| 2020/0085984 A1* | 3/2020 | Randers-Pehrson | A61L 2/10 |

FOREIGN PATENT DOCUMENTS

| WO | 2015012592 A1 | 1/2015 |
|---|---|---|
| WO | 2018089288 A1 | 5/2018 |

OTHER PUBLICATIONS

European Search Report; Application EP21199354; Mar. 25, 2022.
Welch David et al; FAR-UVC Light: A New Tool to Control the Spread of Airborne Mediated Microbial Diseases; Scientific Reports vol. 8 No. 2752; Dec. 1, 2018.

* cited by examiner

*Primary Examiner* — Kevin Joyner
(74) *Attorney, Agent, or Firm* — MH2 Technology Law Group LLP

(57) ABSTRACT

Systems and methods are provided for disinfection. One embodiment is an apparatus that includes a disinfecting device. The disinfecting device includes a shell configured to rotate about an axis, ultraviolet emitters that are configured to emit UV light, and rotational couplings that couple the UV emitters to the shell, and provide for multi-axial rotation of the UV emitters relative to the shell.

20 Claims, 12 Drawing Sheets

ROTATING DISINFECTING DEVICE THAT INCLUDES ULTRAVIOLET EMITTERS

RELATED APPLICATIONS

This non-provisional patent application claims priority to U.S. Provisional Patent Application No. 63/089,112, filed on Oct. 8, 2020.

FIELD

The disclosure relates to the field of disinfection, and in particular, to disinfecting enclosed spaces such as the interior of an aircraft.

BACKGROUND

Enclosed spaces present a difficulty with respect to preventing infection, because the interior of an enclosed space is shared by all occupants of that enclosed space. Furthermore, many enclosed spaces, even those that are particularly small, such as aircraft or lavatories, receive a high volume of individuals throughout the day. Thus, a potential avenue for infection exists within enclosed spaces, in that infected individuals visiting an enclosed space may contaminate surfaces therein, and these contaminated surfaces become vectors by which other individuals who use the enclosed space can be infected.

Even when an effort is made to clean an enclosed space multiple times per day, the risk of infection can be non-trivial, especially for virulent diseases. Further compounding this issue, many surfaces which become contaminated throughout the day may not be in the direct line of sight of occupants, which reduces the likelihood of cleaning personnel disinfecting those surfaces.

Therefore, it would be desirable to have a method and apparatus that take into account at least some of the issues discussed above, as well as other possible issues.

SUMMARY

Embodiments described herein provide disinfecting devices which house Ultraviolet (UV) emitters on a shell. One or more of the UV emitters are capable of being rotated to adjust their fields of illumination. Furthermore, the shell is capable of rotating (i.e., spinning) in order to rotate the UV emitters, thereby increasing the number and amount of surfaces disinfected by direct transmission of UV light. In one embodiment, the UV emitters, by virtue of their distance from each other, their varied angles of orientation with respect to each other, and their rotation with the shell during disinfecting operations, illuminate a variety of different surfaces within an enclosed space. Thus, the multiple UV emitters illuminate a greater surface area than could be accomplished via a single point source UV emitter. This increases the variety of surfaces bathed in disinfecting UV light, which decreases the chance of the enclosed space becoming contaminated.

One embodiment is an apparatus that includes a disinfecting device. The disinfecting device includes a shell configured to rotate about an axis, ultraviolet emitters that are configured to emit UV light, and rotational couplings that couple the UV emitters to the shell, and provide for multi-axial rotation of the UV emitters relative to the shell.

A further embodiment is an apparatus that includes a disinfecting device. The disinfecting device includes a core member, a shell that surrounds the core member, is configured to rotate around the core member, and is cylindrical and ultraviolet (UV) emitters that are fixedly attached around a circumference of the shell. The disinfecting device also includes UV emitters that are rotationally coupled with the shell, and are configured to rotate on multiple axes in relation to the shell, a motor that spins the shell around the core member, and supports that orient the disinfecting device in an upright position.

A further embodiment is a method for disinfecting an enclosed space. The method includes placing a disinfecting device at a surface within the enclosed space, wherein the disinfecting device includes a shell that rotates about an axis, ultraviolet (UV) emitters attached to the shell that are configured to emit UV light, and rotational couplings that provide multi-axial rotation of one or more of the UV emitters relative to the shell, adjusting orientations of the one or more of the UV emitters via the rotational couplings, activating the UV emitters to emit UV light from the UV emitters, and rotating the shell about the axis while the UV light is emitted.

Other illustrative embodiments (e.g., methods and computer-readable media relating to the foregoing embodiments) may be described below. The features, functions, and advantages that have been discussed can be achieved independently in various embodiments or may be combined in yet other embodiments further details of which can be seen with reference to the following description and drawings.

DESCRIPTION OF THE DRAWINGS

Some embodiments of the present disclosure are now described, by way of example only, and with reference to the accompanying drawings. The same reference number represents the same element or the same type of element on all drawings.

DESCRIPTION

The figures and the following description provide specific illustrative embodiments of the disclosure. It will thus be appreciated that those skilled in the art will be able to devise various arrangements that, although not explicitly described or shown herein, embody the principles of the disclosure and are included within the scope of the disclosure. Furthermore, any examples described herein are intended to aid in understanding the principles of the disclosure, and are to be construed as being without limitation to such specifically recited examples and conditions. As a result, the disclosure is not limited to the specific embodiments or examples described below, but by the claims and their equivalents.

Figure 1A:
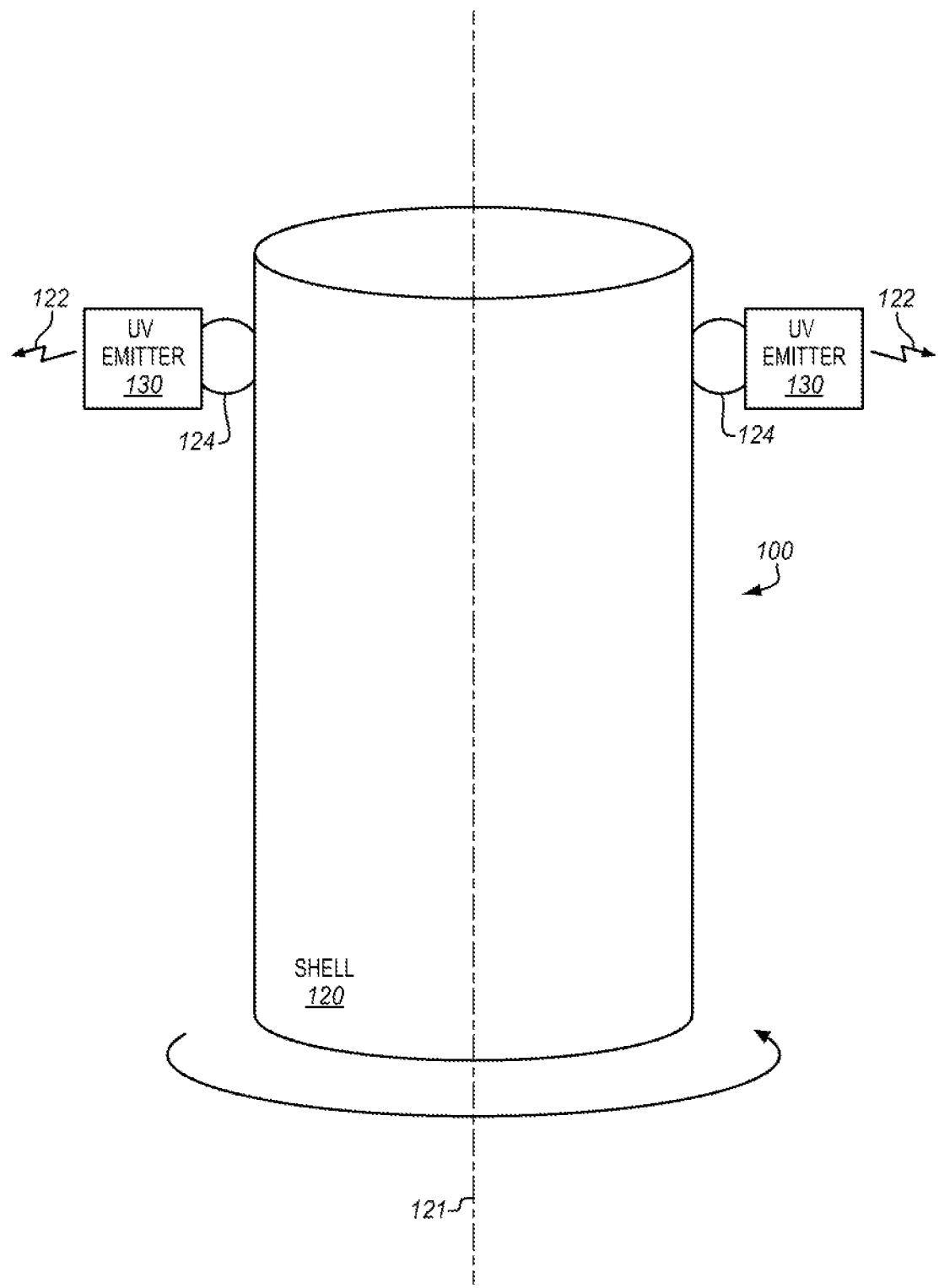
FIG. 1A is a schematic diagram of a disinfecting device in an illustrative embodiment.

FIG. 1A is a schematic diagram of a disinfecting device 100 in an illustrative embodiment. The disinfecting device 100 comprises any suitable system, device, or component capable of performing disinfection by emitting ultraviolet (UV) light. The disinfecting device 100 includes a shell 120, which comprises an elongated housing. The shell 120 may have any suitable cross-sectional shape such as circular, hexagonal, square, etc. The disinfecting device 100 also includes UV emitters 130. The UV emitters 130 comprise components that emit UV light 122 for disinfecting surfaces.

The UV emitters 130 are coupled with the shell 120 via rotational couplings 124. The rotational couplings 124 may comprise ball joints, universal joints, and/or other components that enable the UV emitters 130 to be rotated along multiple axes (e.g., all three axes of X, Y, and Z) relative to the shell 120 in order to change their fields of illumination. While rotational couplings 124 are disposed near the top of the shell 120 in this embodiment, in further embodiments the rotational couplings 124 are additionally or alternatively disposed circumferentially along the middle or bottom of the shell 120.

The shell 120 rotates around an axis 121, such as a central axis of the shell 120. Because the shell 120 is coupled with the UV emitters 130, rotation of the shell 120 causes the UV emitters 130 to rotate and illuminate areas of an enclosed space with UV light 122. The UV light 122 disinfects by deactivating genetic material within viruses and/or bacteria on nearby surfaces, thereby rendering the surfaces inert.

Figure 1B:
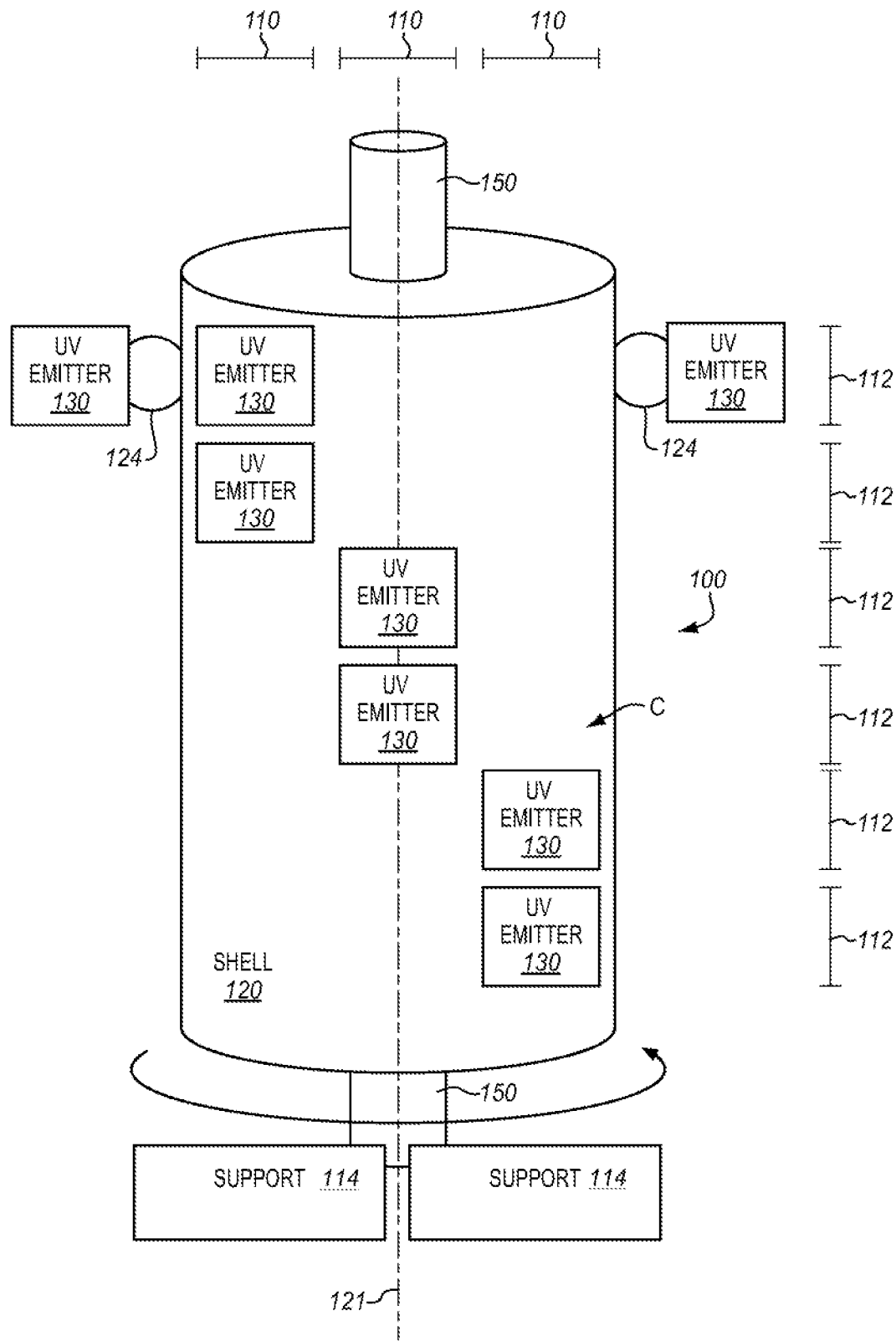
FIG. 1B is a further schematic diagram of a disinfecting device in an illustrative embodiment.

FIG. 1B is a schematic diagram of a disinfecting device 100 in an illustrative embodiment. FIG. 1B depicts further components of a disinfecting device 100 of FIG. 1A in one embodiment. In this embodiment, the disinfecting device 100 includes a core member 150. The core member 150 is an elongated body. In this embodiment, a centerline of the core member 150 defines the axis 121. In one embodiment, the core member 150 is a cylinder formed from a material such as a metal, a plastic, a composite material, etc. In this embodiment, the shell 120 is configured to rotate about the axis 121 in relation to the core member 150. The shell 120 may have a hollow interior that surrounds at least a portion of the core member 150. For example, shell 120 may comprise a hollow cylinder that is disposed around the core member such that the shell 120 and the core member 150 are concentric.

In this embodiment, additional ones of UV emitters 130 are attached to a circumference C of the shell 120, and may for example be distributed radially along the circumference. Each of these UV emitters 130 occupies a unique combination of vertical position 112 and radial position 110. Thus, when shell 120 is spun, the UV emitters 130 that are attached to the circumference of the shell 120 each provide a different field of illumination.

The core member 150 is held up by supports 114 (e.g., legs, wheels, etc.), which retain the core member 150 in an upright position. This ensures that shell 120 does not contact a floor or other surface during rotation, which in turn prevents the rotation of the shell 120 from causing movement or jostling of the disinfecting device 100.

Figure 2:
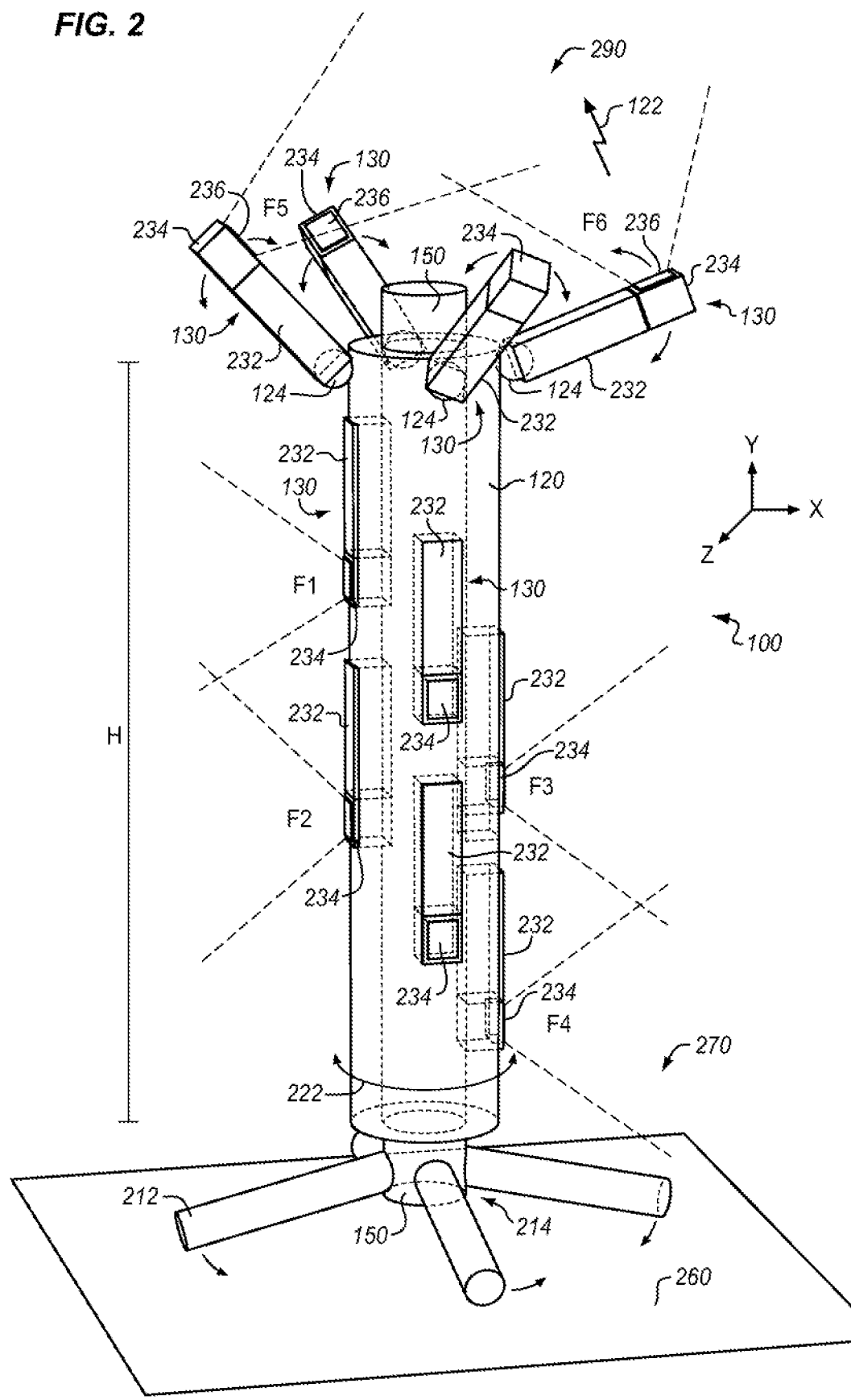
FIGS. 2-4 depict a disinfecting device in an illustrative embodiment.
Figure 3:
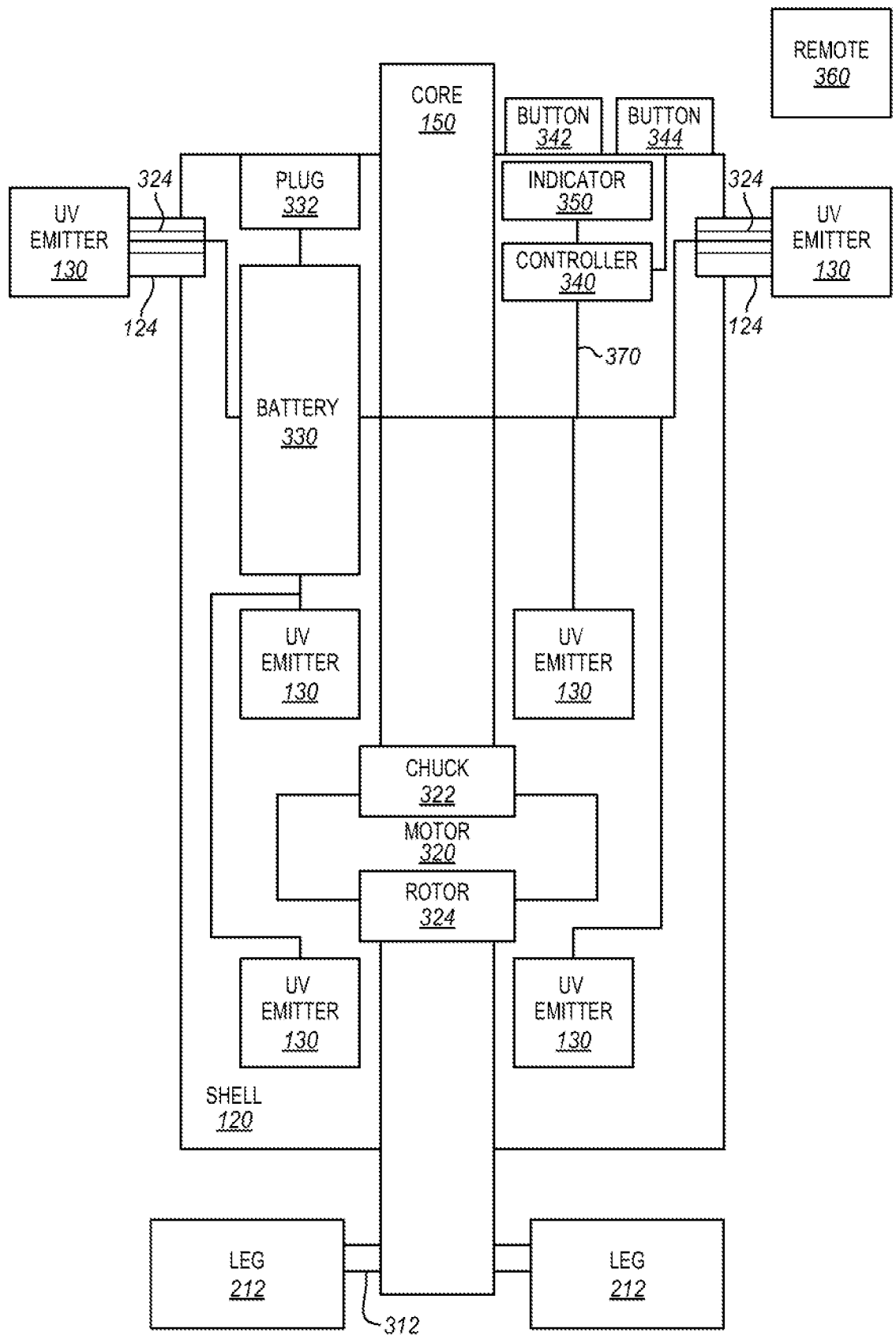
Figure 4:
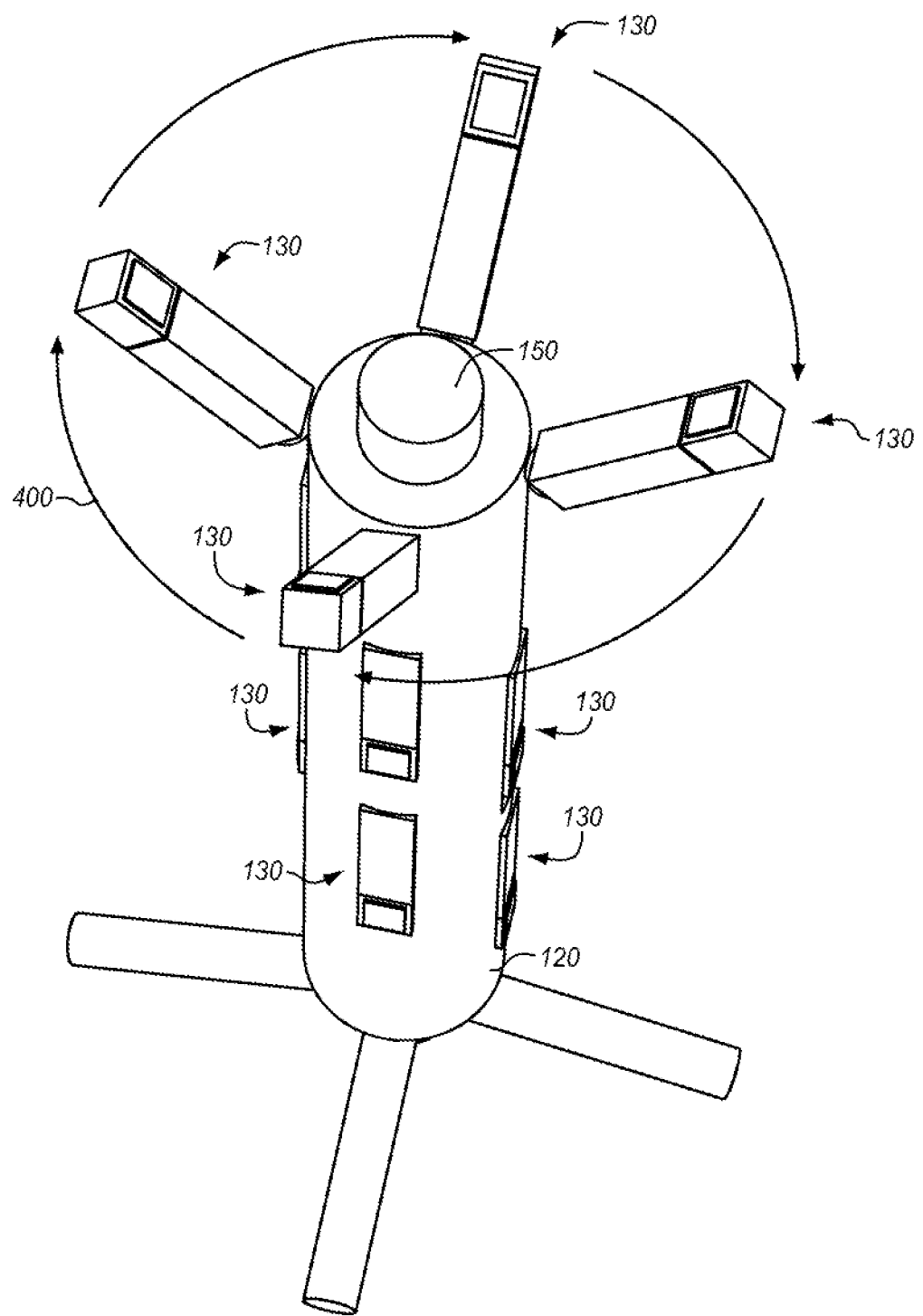

FIGS. 2-4 depict the disinfecting device 100 in an illustrative embodiment. Disinfecting device 100 is placed atop a surface 260 in an upright position 290, which may comprise a boundary (e.g., a floor) of an enclosed space 270 or an object within an enclosed space 270. For example, disinfecting device 100 may be placed on a surface such as an aisle of an aircraft. In such embodiments, the disinfecting device 100 is dimensioned for placement within the aisle.

In this embodiment, the UV emitters 130 are physically coupled with the shell 120. Some of the UV emitters 130 are rotationally coupled with the shell 120 via the rotational couplings 124 in one embodiment. Other UV emitters 130 are fixedly attached to the shell 120, and are not mated with the rotational couplings 124.

In this embodiment, each of the UV emitters 130 includes a head 234 that houses a UV Light Emitting Diode (LED), and a body 232 that houses a power supply. Each head 234 includes an optical face 236 that is transparent to UV light 122, and that protects a UV LED of the UV emitter 130 from physical damage (e.g., resulting from an impact).

The UV emitters 130 emit the UV light 122 via the optical faces 236. The UV light 122 is absorbed by surfaces in direct line of sight of the optical faces 236 of the heads 234, which deactivates genetic material within viruses and/or bacteria disposed at the surfaces, rendering them inert. In one embodiment, heads 234 emit the UV light 122 at a wavelength of two hundred and twenty two nanometers, which is safe for humans. In such an embodiment, the UV emitters 130 may continue to emit UV light even while the enclosed space 270 is occupied (e.g., by cleaning personnel).

In this embodiment, the UV emitters 130 are arranged in a staggered configuration, such that each of the UV emitters 130 occupies a different vertical position 112 (and optionally radial position 110) at the shell 120. Thus, when the shell 120 is rotated, each UV emitter 130 on the shell covers a different field of illumination when the UV emitters 130 are activated and the shell 120 is rotated.

By adjusting the angle and position of the heads of the UV emitters 130, the UV emitters 130 are capable of illuminating (e.g., directly irradiating) different portions of an enclosed space that are within fields of illumination F1, F2, F3, F4, F5, F6, etc. To further increase the amount of surface area disinfected by disinfecting device 100, shell 120 rotates in direction 222 about the core member 150.

In one embodiment, both the shell 120 and the core member 150 are made of rigid material 214 (e.g., plastic, metal, ceramic, Carbon Fiber Reinforced Polymer (CFRP), etc.). Legs 212 comprise four legs that are each pivotally attached to core member 150, and in this embodiment are rotatably attached to core member 150 to facilitate collapsing the disinfecting device 100. The legs 212 maintain the disinfecting device 100 in the upright position 290, and prevent tipping of the disinfecting device 100. Specifically, the legs 212 have a length such that tipping of the disinfecting device 100 is prevented regardless of torque that would be applied by the various possible orientations of the UV emitters 130 at the disinfecting device 100.

FIG. 3 is a block diagram representing internal components of the disinfecting device 100 of FIG. 2 in an illustrative embodiment. Many of these internal components include electronics within the shell 120 that rotate with the shell 120. By integrating electronics and power systems into the shell 120, these components are continuously spun with the shell 120 without tangling. This enables the shell 120 to be continuously spun without encountering tangled wiring or other issues. According to FIG. 3, a power system in the form of a battery 330 is disposed within the shell 120. Battery 330 powers the UV emitters 130, including those rigidly affixed to the shell 120 and those rotatably affixed to the shell 120 via rotational couplings 124. Battery 330 is electrically coupled with a plug 332. The plug 332 enables the battery 330 to be powered via an electrical system (e.g., via an outlet) in order to recharge the disinfecting device 100 during idle periods.

FIG. 3 also makes clear that the rotational couplings 124 define passages that enable the wiring 370 to pass through to the UV emitters 130. The wiring 370 includes excess length, which enables the wiring 370 to accommodate any changes in shape caused by repositioning the rotational couplings 124 during operation, without the wiring 370 being pinched or placed into tension. Because all electrical components of the disinfecting device 100 are integrated into the shell 120, rotation of the shell 120 does not cause twisting of wiring 370. This enables the shell 120 to rotate infinitely in a clockwise or counterclockwise direction in response to forces applied by motor 320.

In one embodiment, motor 320 is disposed within the shell 120 or otherwise integrated into the shell 120, and is rotatably secured to core member 150 via a chuck 322, rod, bolt, or other component. Motor 320 may itself include a rotor 324 which core member 150 is integrated with or mechanically coupled with. In such an embodiment, spinning the rotor 324 of the motor 320 spins the core member 150 (e.g., by interlocking teeth at the motor with teeth in the core member 150). Motor 320 may drive the shell 120 at any suitable rotational rate about core member 150. However, to conserve energy, motor 320 may rotate shell 120 at a rate between one revolution per second and one revolution per minute. Battery 330 powers the motor 320.

Controller 340 dictates the operations of the disinfecting device 100. In one embodiment, the controller 340 includes logic for switching to the battery 330 when power is interrupted at plug 332. In a further embodiment the controller 340 reports a low battery state by monitoring the battery 330 and lighting the indicator 350 if an amount of energy stored in the battery 330 is below a threshold level (e.g., twenty percent). In a further embodiment, the controller 340 activates the UV emitters 130 and motor 320 for a limited time period in response to receiving input from a user (e.g., the pressing of an "on" button at the controller 340). This ensures that disinfection continues for a predefined disinfection period (e.g., fifteen minutes), while also ensuring that battery power is not wasted after disinfection has been completed. In one embodiment, controller 340 is implemented as custom circuitry, as a hardware processor executing programmed instructions stored in memory, or some combination thereof.

Button 342 and button 344 provide input to controller 340, which may be utilized to activate or deactivate motor 320, UV emitters 130, etc. Furthermore, in some embodiments, a remote 360 transmits wireless signals to the controller 340 in order to direct the operations of the disinfecting device 100. A remote 360 may be particularly desirable in embodiments where motor 320 is set to spin at a high rate (e.g., between one revolution per second and one revolution per five seconds, or faster), as it may become difficult to manually reach buttons 342 and 344 in such embodiments.

FIG. 3 further illustrates that, in one embodiment, each leg 212 is pivotally attached to the core member 150 via a hinge 312. The hinges 312 are held in position by friction, wherein an amount of force required to change a position of the hinges 312 is greater than an amount of force equal to the weight of the disinfecting device 100. This prevents the disinfecting device 100 from collapsing under its own weight when deployed.

FIG. 4 is a top perspective view of the disinfecting device 100 of FIGS. 2-3 in an illustrative embodiment. In this embodiment, the shell 120 of the disinfecting device 100 rotates in a clockwise direction 400 in response to motor 320 interacting with core member 150. FIG. 4 makes clear the increased amount of rotational freedom granted to UV emitters 130 located at the top of the disinfecting device 100, as these UV emitters 130 are permitted by rotational couplings 124 to be adjusted to a wide variety of angles and positions.

Figure 5:
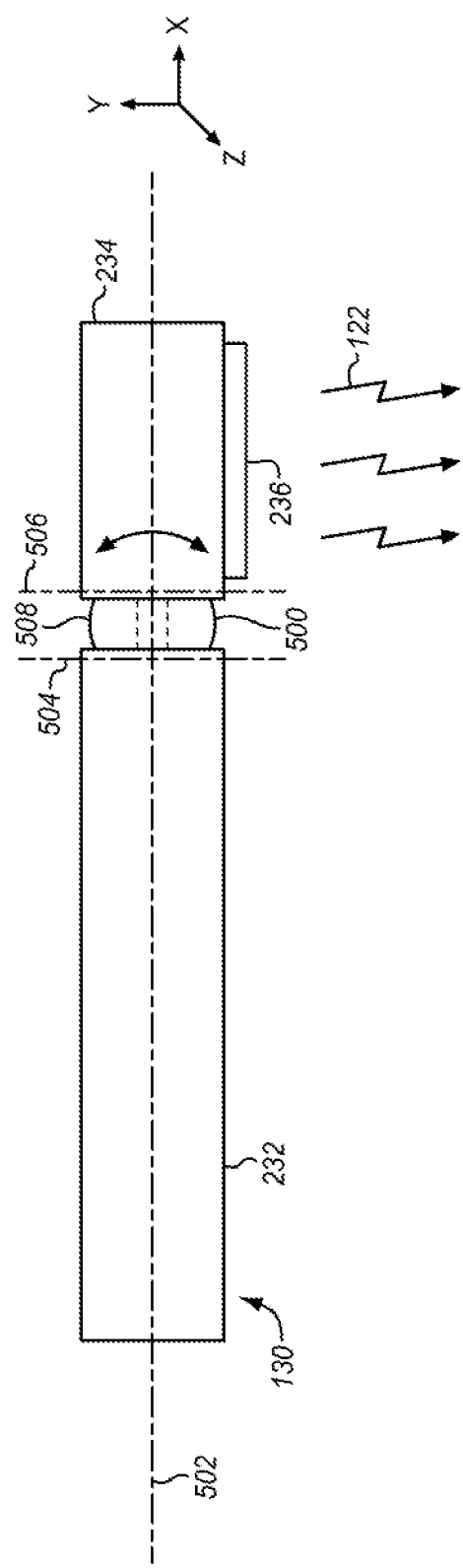
FIGS. 5-7 depict a UV emitter with a head that is adjustable and that may be integrated into a disinfecting device in an illustrative embodiment.
Figure 6:
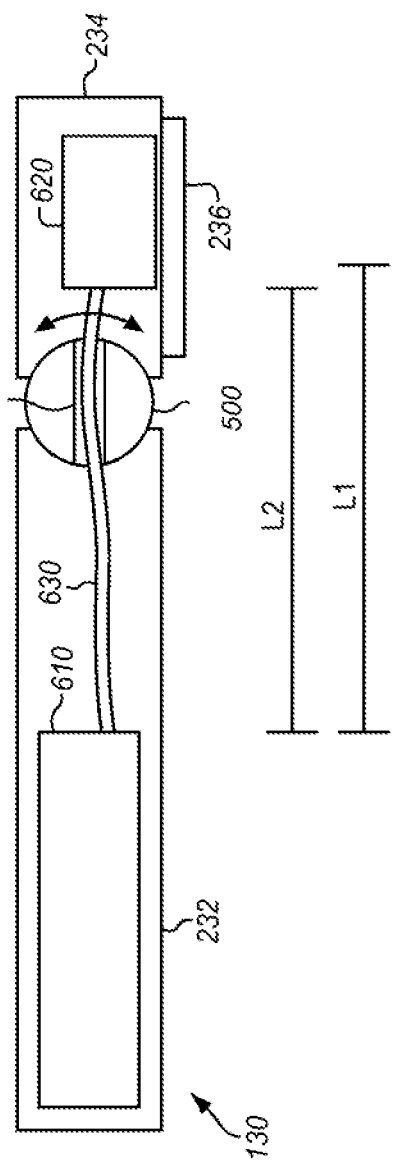
Figure 7:
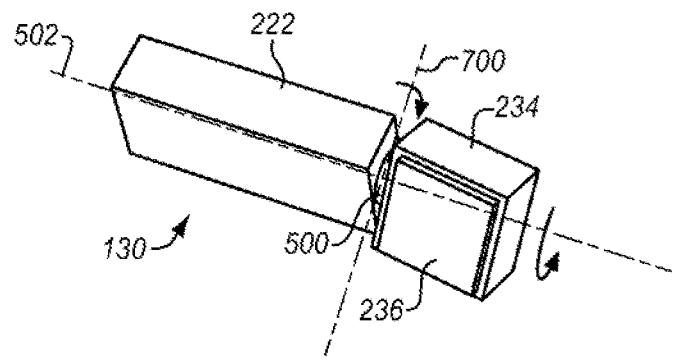

FIGS. 5-7 depict a UV emitter 130 with a head 234 that is adjustable and that may be integrated into a disinfecting device 100 in an illustrative embodiment. The UV emitters 130 of the disinfecting device 100 of FIG. 2 may comprise adjustable emitters of the kind shown in FIGS. 5-7, in order to further enhance the ability of the disinfecting device 100 to irradiate a greater amount of surfaces within an enclosed space with UV light 122. In this manner, even UV emitters 130 that are affixed to the shell 120 of a disinfecting device 100 are capable of adjusting their fields of illumination, which enhances the ability of the disinfecting device 100 to perform disinfection in a variety of enclosed spaces.

FIG. 5 illustrates a UV emitter 130 which includes a body 232. The body 232 is coupled with a head 234 having an optical face 236 via a neck 500 (e.g., comprising a ball joint 508, a universal joint, etc.). The optical face 236 emits UV light 122. The neck 500 enables rotation of the head 234 relative to the body 232 along multiple axes (e.g., along X, Y, and/or Z or some subset thereof, along a central axis 502 of the body 232, along axis 504 and/or axis 506, etc.). In one embodiment, the neck 500 is tightly coupled against head 234 and body 232. Thus, a greater amount of force than the weight of head 234 or body 232 is necessary to overcome friction between head 234, body 232, and/or neck 500 in order to reorient the neck 500. This prevents the head 234 from sagging or otherwise changing position after it has been rotated to a desired angle via the neck 500.

FIG. 6 is a section cut view of the UV emitter 130, and illustrates that body 232 houses a power supply 610, which converts received electrical energy to a desired voltage (e.g., twenty-four volts) and/or amperage for use by a Light Emitting Diode (LED) 620. FIG. 6 further illustrates internal wiring 630 that electrically connects power supply 610 to LED 620. Internal wiring 630 reaches the LED 620 via passage 510 in the neck 500. That is, for each of the UV emitters 130, the neck 500 defines a passage 510 that houses the internal wiring 630 coupling an LED 620 of the UV emitter 130 to a power supply 610 of the UV emitter 130.

The length L1 of internal wiring 630 when held taut exceeds a length L2 corresponding to a distance between the LED 620 and the power supply 610. This excess length enables the internal wiring 630 to move to accommodate repositioning of the neck 500, without being pinched or placed into tension.

FIG. 7 provides a perspective view wherein a head 234 of an additional UV emitter 130 has been adjusted to a new position via neck 500. As shown in FIG. 7, the head 234 of the additional UV emitter 130 has been rotated about central axis 502 of the body, as well as axis 700.

Figure 8:
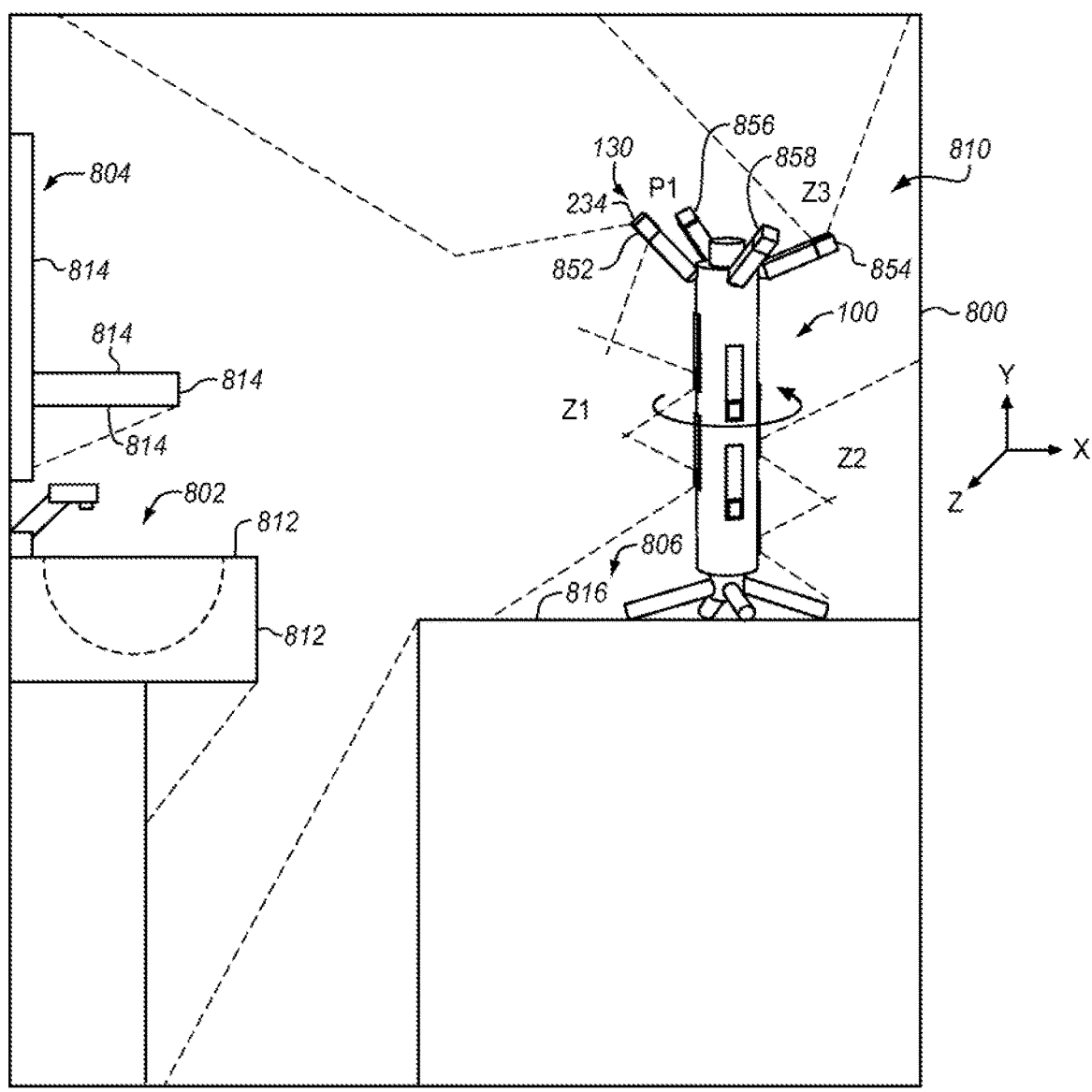
FIGS. 8-9 depict a disinfecting device that rotates within an enclosed space in an illustrative embodiment.
Figure 9:
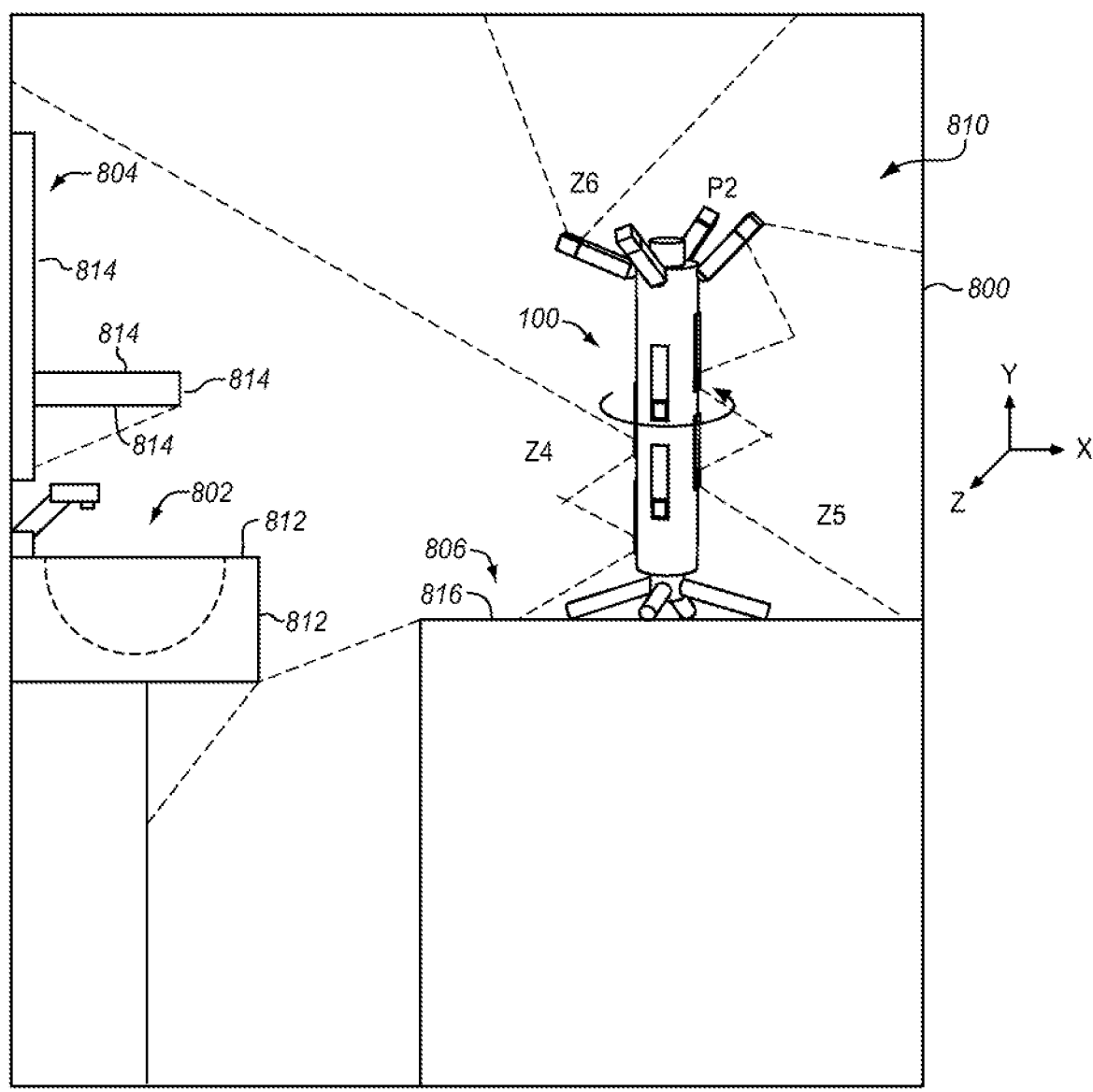
Figure 10:
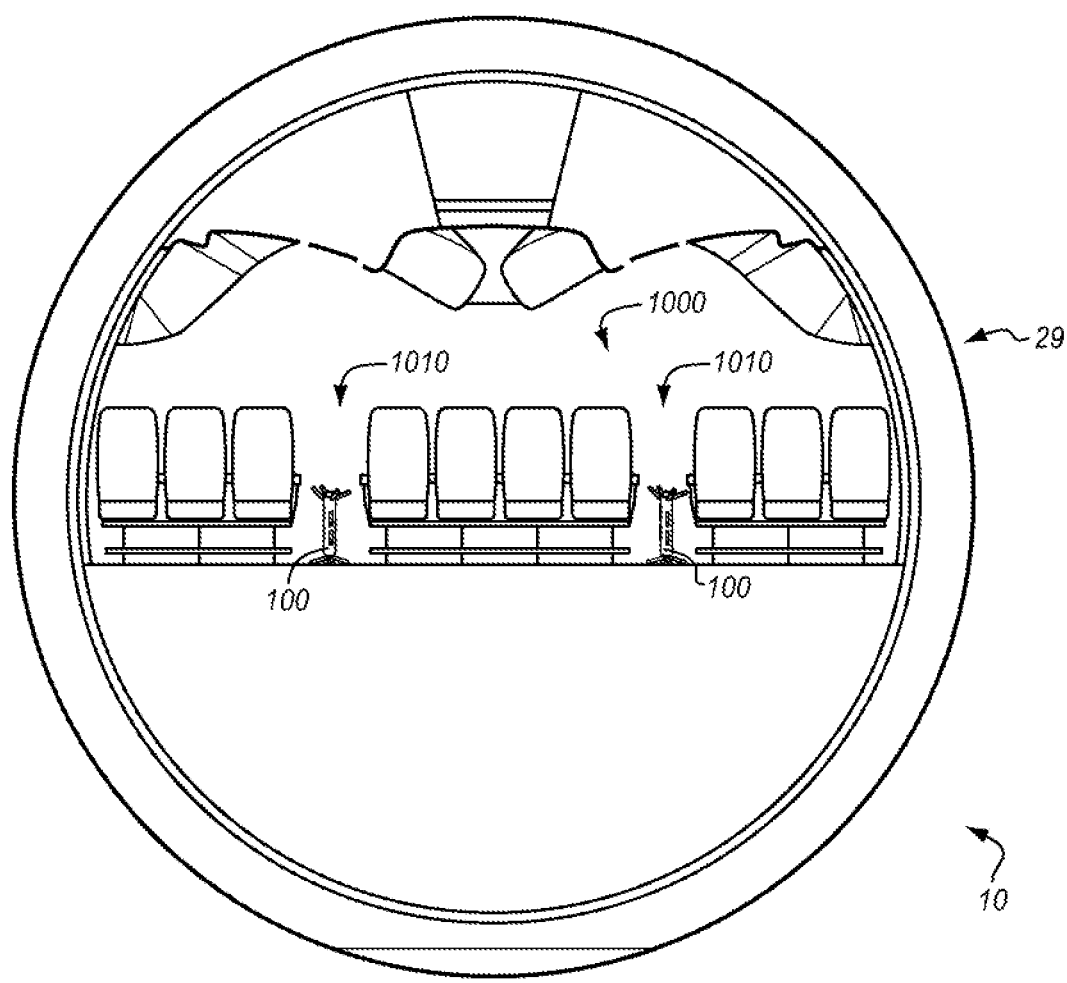
FIG. 10 depicts disinfecting devices located within a cabin of an aircraft in an illustrative embodiment.

While the above FIGS. discuss the composition of a disinfecting device 100 and UV emitters 130 within a disinfecting device 100, the following FIGS. 8-10 depict placement and operation of disinfecting devices 100 in order to facilitate disinfection of surfaces in illustrative embodiments.

FIG. 8 depicts a disinfecting device 100 that rotates within an enclosed space 810 of a room 800 in an illustrative embodiment. The enclosed space 810 includes multiple objects 802, 804, and 806, having surfaces 812, 814, and 816 respectively. Heads 234 of the UV emitters 130 of the disinfecting device 100 are vertically and horizontally separated from each other, and may be arranged at differing angles along axes of X, Y, and Z. This separation, combined with the ability to adjust the heads 234 to unique orientations 852, 854, 856, and 858, enables the heads 234 to emit UV light that directly illuminates the surfaces 812, 814, and 816 in different volumes Z1, Z2, and Z3, even though the surfaces 812, 814, and 816 are disposed at different locations and face in different directions. Phrased another way, each head 234 directly illuminates a different combination of surfaces and/or portions of the objects 802, 804, and 806. Because UV light does not reflect but rather is absorbed by most surfaces, direct illumination of the surfaces 812, 814, and 816 via the heads 234 is highly desirable. This ability to disinfect all of the surfaces 812, 814, and 816 is not possible from any point source of UV light. Thus, disinfecting device 100 provides a technical benefit by enabling a greater amount of surfaces, arranged at a greater amount of angles, to be disinfected via the installation of a single disinfecting device.

FIG. 9 illustrates that, after rotation of the disinfecting device 100, new volumes Z4, Z5, and Z6 are directly illuminated with UV light. This further increases the amount of surface area disinfected by the disinfecting device during operation.

FIG. 10 depicts multiple instances of disinfecting devices 100 located within a cabin 1000 in a barrel section 29 of an aircraft 10 in an illustrative embodiment. In this embodiment, the disinfecting devices 100 are placed in aisles 1010 in between flights (e.g., while cargo is being loaded or unloaded pre- or post-flight). The disinfecting devices 100 are activated to disinfect surfaces at the cabin 1000. In one embodiment where the disinfecting devices 100 emit UV light having a wavelength of two hundred and twenty two nanometers, the disinfecting devices 100 have no deleterious effects on humans, and may be activated in the presence of humans (e.g., cleaning staff) for any suitable purpose. This enables cleaning staff to disinfect a portion of an aircraft via disinfecting devices 100, while performing other duties (e.g., vacuuming, trash removal, etc.) manually.

Illustrative details of the operation of disinfecting device 100 will be discussed with regard to FIG. 11. Assume, for this embodiment, that an aircraft awaits cleaning in between flights during an ongoing health crisis that proceeds for a period of multiple days.

Figure 11:
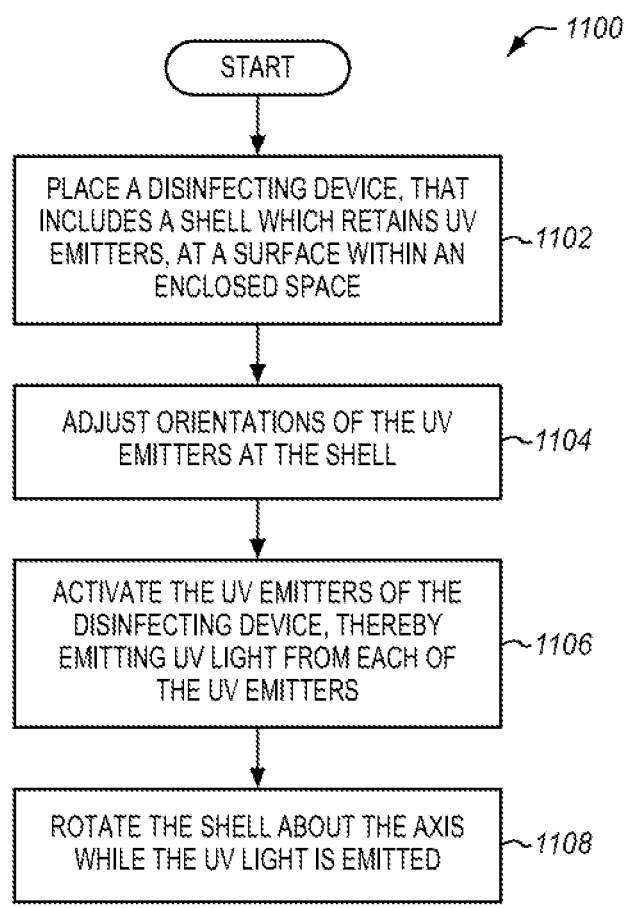
FIG. 11 is a flowchart illustrating a method for disinfecting an enclosed space in an illustrative embodiment.

FIG. 11 is a flowchart illustrating a method 1100 for disinfecting an enclosed space in an illustrative embodiment, and may be performed in between flights of an aircraft in order to disinfect a cabin of the aircraft as desired. The steps of method 1100 are described with reference to disinfecting device 100 of FIG. 1, but those skilled in the art will appreciate that method 1100 may be performed in other systems and/or devices. The steps of the flowcharts described herein are not all inclusive and may include other steps not shown. The steps described herein may also be performed in an alternative order.

Method 1100 includes placing 1102 a disinfecting device 100, that includes a shell 120 which retains UV emitters 130, at a surface 816 within an enclosed space 810. In one embodiment, this comprises configuring the disinfecting device 100 from an undeployed state (closed) to a deployed state (open) by pivoting the legs 212 about hinges 312, thereby enabling the legs 212 to stably support a weight of the disinfecting device 100. The disinfecting device 100 may be placed upon any stable surface (e.g., a level surface). However, in many embodiments a surface will be chosen from which disinfecting device 100 is capable of illuminating a large portion of the enclosed space 810.

Method 1100 further includes adjusting 1104 orientations of the UV emitters 130 at the shell 120. In one embodiment, this comprises manually adjusting the orientations of heads 234 relative to bodies 232 of the UV emitters 130, pivoting some of the UV emitters 130 from the shell 120 via the rotational couplings 124, etc. in order to ensure that heads 234 of different ones of UV emitters 130 illuminate different fields of illumination. That, is, adjusting orientations of the heads increases an amount of surface area of the enclosed space exposed to the UV light. In one embodiment, the orientations of the UV emitters 130 are adjusted such that each UV emitter 130 illuminates a different volume within the enclosed space (e.g., sones Z1, Z2, Z3, et. seq.) when the shell is spun by a full rotation. In further embodiments, the adjusting is performed automatically by controller 340 according to a preprogrammed set of desired orientations for the enclosed space (e.g., by operating rotational couplings 124 that are powered).

Method 1100 further includes activating 1106 the UV emitters 130 of the disinfecting device 100, thereby emitting UV light 122 from each of the UV emitters 130. Activating the UV emitters 130 may be performed by controller 340 completing a circuit that causes electricity to flow between battery 330 and the UV emitters 130. In one embodiment, emitting UV light comprises emitting UV light at a wavelength of two hundred and twenty two nanometers.

In one embodiment, activating 1106 comprises pressing a button 342 that is coupled with controller 340, which causes the controller 340 to close a switch, thereby enabling electrical power to flow from battery 330 to the UV emitters 130. This causes the LEDs 620 of the UV emitters to radiate UV light 122. The UV light is absorbed by bacteria and viruses on surfaces 812, 814, and 816 within the enclosed space 810, resulting in energy that damages genetic information within the bacteria and viruses, rendering them inert. In yet another embodiment, a remote 360 transmits an instruction to the controller 340 to activate the UV emitters 130.

Method 1100 further includes rotating 1108 the shell 120 about the axis 121 while the UV light is emitted. In one embodiment, this comprises activating a motor 320 of the disinfecting device 100 that spins the shell 120 while the UV light 122 is emitted. Activating the motor 320 may be performed by controller 340 completing a circuit that causes electricity to flow between battery 330 and the motor 320. Furthermore, activating the motor 320 and activating the UV emitters 130 may be performed concurrently. In one embodiment, a button 344 coupled with the controller 340 is pressed, which causes the controller 340 to enable electrical power to flow from battery 330 to the motor 320. In a further embodiment, the pressing of button 342, or the activation of the UV emitter 130 by another means, also activates the motor and initiates rotation or spinning of the shell 120. In yet another embodiment, a remote 360 transmits an instruction to the controller 340 to activate the motor 320.

Method 1100 provides a technical benefit by enabling a single portable disinfecting device to illuminate objects from a variety of different fields of illumination, thereby increasing an overall surface area of an enclosed space being disinfected from a single location.

EXAMPLES

In the following examples, additional processes, systems, and methods are described in the context of a disinfecting device for an enclosed space.

Figure 12:
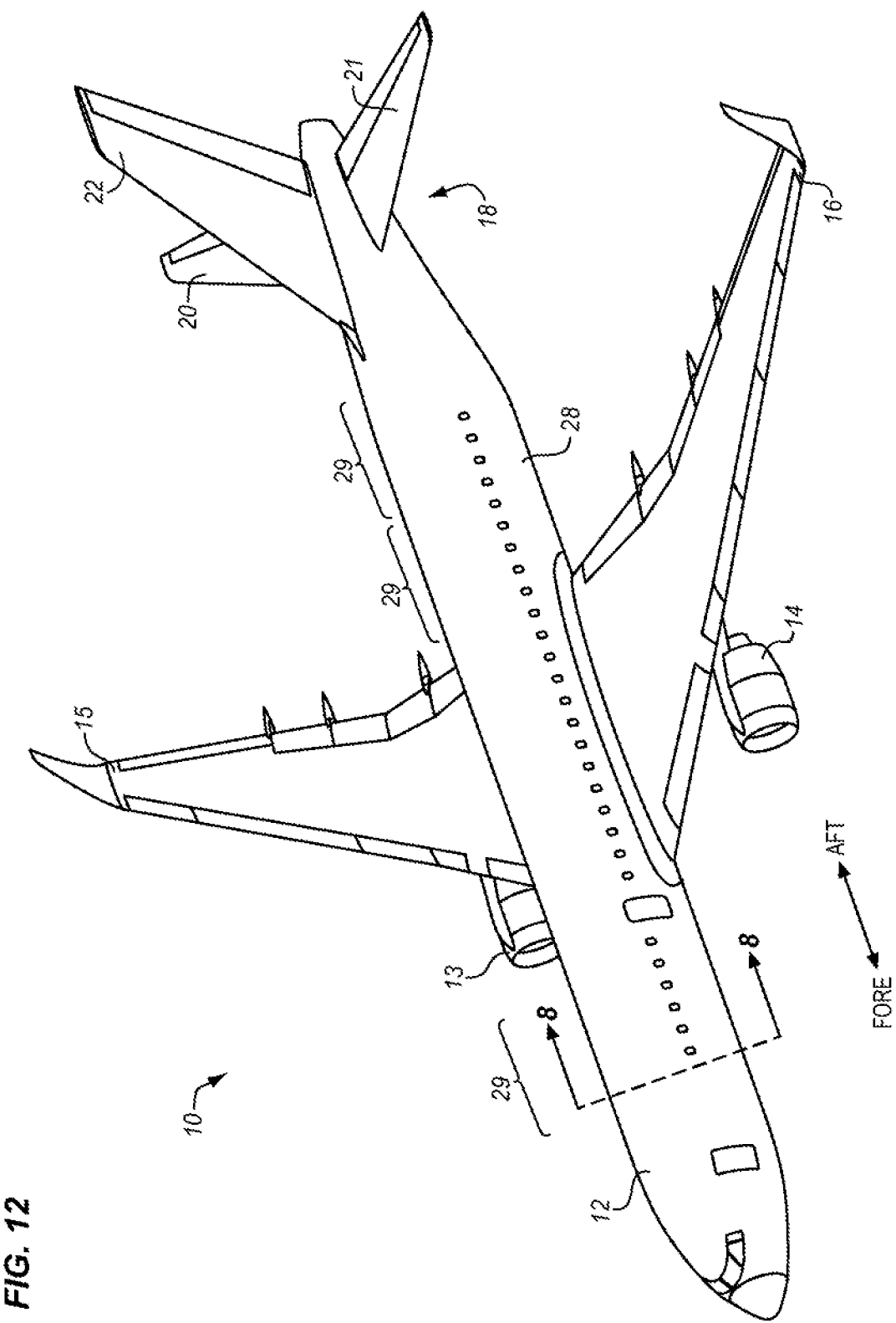
FIG. 12 illustrates an aircraft in an illustrative embodiment.

Turning now to FIG. 12, an illustration of an aircraft 10 is depicted for which the systems and methods described herein may be implemented. In this illustrative example, aircraft 10 includes wing 15 and wing 16 attached to fuselage 28 having a nose 12. Aircraft 10 includes engine 13 attached to wing 15 and engine 14 attached to wing 16. Tail section 18 is also attached to fuselage 28. Horizontal stabilizer 20, horizontal stabilizer 21, and vertical stabilizer 22 are attached to tail section 18 of fuselage 28. The fuselage 28 itself is formed from multiple barrel sections 29 which have been joined together. In this embodiment, three barrel sections 29 are labeled, but any suitable number of barrel sections 29 may be utilized to form the fuselage 28 as a matter of design choice.

Figure 13:
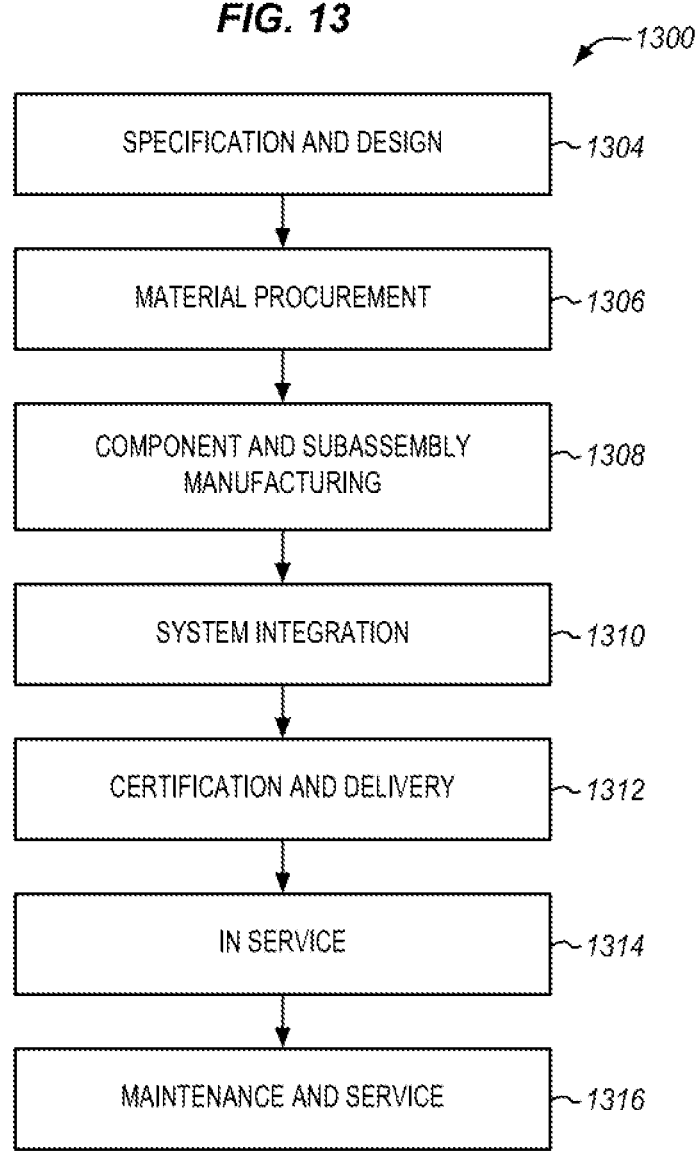
FIG. 13 is a flow diagram of aircraft production and service methodology in an illustrative embodiment.
Figure 14:
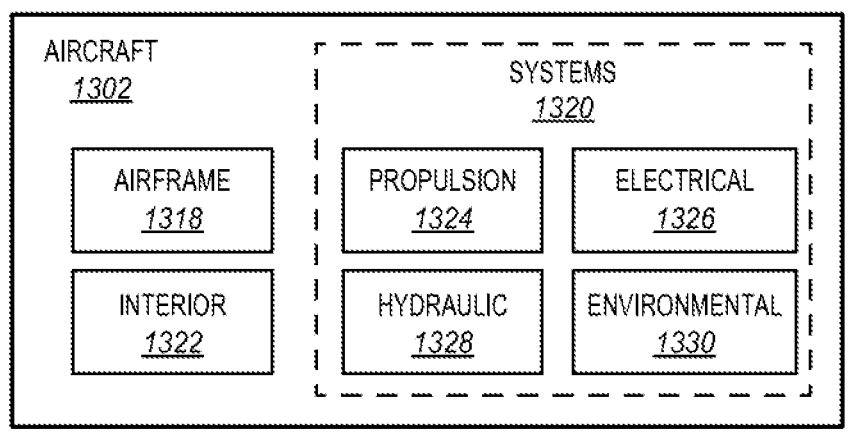
FIG. 14 is a block diagram of an aircraft in an illustrative embodiment.

Referring more particularly to the drawings, embodiments of the disclosure may be described in the context of aircraft manufacturing and service in method 1300 as shown in FIG. 13 and an aircraft 1302 as shown in FIG. 13. During pre-production, method 1300 may include specification and design 1304 of the aircraft 1302 and material procurement 1306. During production, component and subassembly manufacturing 1308 and system integration 1310 of the aircraft 1302 takes place. Thereafter, the aircraft 1302 may go through certification and delivery 1312 in order to be placed in service 1314. While in service by a customer, the aircraft 1302 is scheduled for routine work in maintenance and service 1316 (which may also include modification, reconfiguration, refurbishment, and so on). Apparatus and methods embodied herein may be employed during any one or more suitable stages of the production and service described in method 1300 (e.g., specification and design 1304, material procurement 1306, component and subassembly manufacturing 1308, system integration 1310, certification and delivery 1312, service 1314, maintenance and service 1316) and/or any suitable component of aircraft 1302 (e.g., airframe 1318, systems 1320, interior 1322, propulsion system 1324, electrical system 1326, hydraulic system 1328, environmental system 1330).

Each of the processes of method 1300 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 13, the aircraft 1302 produced by method 1300 may include an airframe 1318 with a plurality of systems 1320 and an interior 1322. Examples of systems 1320 include one or more of a propulsion system 1324, an electrical system 1326, a hydraulic system 1328, and an environmental system 1330. Any number of other systems may be included. Although an aerospace example is shown, the principles of the invention may be applied to other industries, such as the automotive industry.

As already mentioned above, apparatus and methods embodied herein may be employed during any one or more of the stages of the production and service described in method 1300. For example, components or subassemblies corresponding to component and subassembly manufacturing 1308 may be fabricated or manufactured in a manner similar to components or subassemblies produced while the aircraft 1302 is in service. Also, one or more apparatus embodiments, method embodiments, or a combination thereof may be utilized during the subassembly manufacturing 1308 and system integration 1310, for example, by substantially expediting assembly of or reducing the cost of an aircraft 1302. Similarly, one or more of apparatus embodiments, method embodiments, or a combination thereof may be utilized while the aircraft 1302 is in service, for example and without limitation during the maintenance and service 1316. Thus, the invention may be used in any stages discussed herein, or any combination thereof, such as specification and design 1304, material procurement 1306, component and subassembly manufacturing 1308, system integration 1310, certification and delivery 1312, service 1314, maintenance and service 1316 and/or any suitable component of aircraft 1302 (e.g., airframe 1318, systems 1320, interior 1322, propulsion system 1324, electrical system 1326, hydraulic system 1328, and/or environmental system 1330).

In one embodiment, a part comprises a portion of airframe 1318, and is manufactured during component and subassembly manufacturing 1308. The part may then be assembled into an aircraft in system integration 1310, and then be utilized in service 1314 until wear renders the part unusable. Then, in maintenance and service 1316, the part may be discarded and replaced with a newly manufactured part. Inventive components and methods may be utilized throughout component and subassembly manufacturing 1308 in order to manufacture new parts.

Any of the various control elements (e.g., electrical or electronic components) shown in the figures or described herein may be implemented as hardware, a processor implementing software, a processor implementing firmware, or some combination of these. For example, an element may be implemented as dedicated hardware. Dedicated hardware elements may be referred to as "processors", "controllers", or some similar terminology. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, a network processor, application specific integrated circuit (ASIC) or other circuitry, field programmable gate array (FPGA), read only memory (ROM) for storing software, random access memory (RAM), non-volatile storage, logic, or some other physical hardware component or module.

Also, a control element may be implemented as instructions executable by a processor or a computer to perform the functions of the element. Some examples of instructions are software, program code, and firmware. The instructions are operational when executed by the processor to direct the processor to perform the functions of the element. The instructions may be stored on storage devices that are readable by the processor. Some examples of the storage devices are digital or solid-state memories, magnetic storage media such as a magnetic disks and magnetic tapes, hard drives, or optically readable digital data storage media.

Although specific embodiments are described herein, the scope of the disclosure is not limited to those specific embodiments. The scope of the disclosure is defined by the following claims and any equivalents thereof.

What is claimed is:

1. An apparatus comprising a disinfecting device, the disinfecting device comprising:
    a shell configured to rotate about an axis;
    a central core member that is surrounded by the shell and that defines the axis, wherein the central core member remains unmoving while the shell rotates about the axis;
    ultraviolet (UV) emitters that are configured to emit UV light, wherein each of the UV emitters comprises a body that retains a power supply, and a head that retains a UV Light Emitting Diode (LED); and
    rotational couplings that couple the UV emitters to the shell, and provide for multi-axial rotation of the UV emitters relative to the shell.

2. The apparatus of claim 1 further comprising:
    UV emitters that are affixed to the shell around a circumference of the shell, and that are disposed at varying radial positions and vertical positions along the circumference; and
    supports that retain the disinfecting device in an upright position.

3. The apparatus of claim 1 further comprising:
    a motor that is configured to rotate the shell about the axis, and is disposed within the shell.

4. The apparatus of claim 3 further comprising:
    a battery disposed within the shell that is configured to power the motor.

5. The apparatus of claim 1 wherein:
    the head includes a neck that permits multi-axial rotation of the head relative to the body.

6. The apparatus of claim 5 wherein:
    the UV LED at each of the heads is protected by an optical face that is transparent to UV light.

7. The apparatus of claim 1 wherein:
    the UV emitters emit UV light at a wavelength of two hundred and twenty two (222) nanometers.

8. An apparatus comprising a disinfecting device, the disinfecting device comprising:
    a central core member;
    a shell that surrounds the central core member, is configured to rotate around the central core member, and is cylindrical;
    ultraviolet (UV) emitters that are fixedly attached around a circumference of the shell wherein each of the UV emitters comprises a body that retains a power supply, and a head that retains a UV Light Emitting Diode (LED);
    UV emitters that are rotationally coupled with the shell, and are configured to rotate on multiple axes in relation to the shell;
    a motor that spins the shell around the central core member; and
    supports that orient the disinfecting device in an upright position.

9. The apparatus of claim 8 wherein:
    the UV emitters that are fixedly attached around the circumference of the shell are distributed radially along the shell.

10. The apparatus of claim 8 further comprising:
    a battery disposed within the shell.

11. The apparatus of claim 10 wherein:
    the battery powers the motor.

12. The apparatus of claim 8 wherein:
    the supports comprise legs that are each pivotally attached to the central core member.

13. The apparatus of claim 8 wherein:
    the UV emitters that are rotationally coupled with the shell are attached to the shell via rotational couplings.

14. The apparatus of claim 8 wherein:
    the UV emitters emit UV light at a wavelength of two hundred and twenty two (222) nanometers.

15. The apparatus of claim 8 wherein:
    the disinfecting device is dimensioned for placement within an aisle of an aircraft.

16. A method for disinfecting an enclosed space, the method comprising:
    placing a disinfecting device at a surface within the enclosed space, wherein the disinfecting device includes a shell that rotates about an axis, a central core member that is surrounded by the shell and that defines the axis, wherein the central core member remains unmoving while the shell rotates about the axis, ultraviolet emitters attached to the shell that are configured to emit UV light using a power supply within each UV emitter, and rotational couplings that provide multi-axial rotation of one or more of the UV emitters relative to the shell;
    adjusting orientations of the one or more of the UV emitters via the rotational couplings; activating the UV emitters to emit UV light from the UV emitters; and rotating the shell about the axis while the UV light is emitted.

17. The method of claim 16 wherein:
    the enclosed space is a cabin of an aircraft.

18. The method of claim 16 further comprising:
    powering a motor that rotates the shell via a battery within the shell.

19. The method of claim 16 wherein:
    adjusting orientations of the UV emitters at the shell such that each UV emitter illuminates a different volume within the enclosed space.

20. The method of claim 16 wherein:
    emitting UV light comprises emitting UV light at a wavelength of two hundred and twenty two (222) nanometers.

* * * * *